United States Patent
Wu

(10) Patent No.: US 6,511,446 B1
(45) Date of Patent: Jan. 28, 2003

(54) MESSAGE BEAD WITH HEAT APPLICATION EFFECT

(76) Inventor: Chia-Hsiung Wu, P.O. Box No.6-57, 3 (TW)

( * ) Notice: Subject to any disclaimer, the term of this patent is extended or adjusted under 35 U.S.C. 154(b) by 0 days.

(21) Appl. No.: 09/987,792

(22) Filed: Nov. 16, 2001

(51) Int. Cl.[7] ................................................. A61H 1/00
(52) U.S. Cl. ............................ 601/15; 601/18; 601/70; 601/71; 601/56
(58) Field of Search ............................. 601/15, 22, 28, 601/49, 56, 57, 64, 65, 67, 70, 80, 128, 129, 131–135

(56) References Cited

U.S. PATENT DOCUMENTS

| | | | | |
|---|---|---|---|---|
| 4,577,625 A | * | 3/1986 | Lohati et al. | 601/128 |
| 4,722,326 A | * | 2/1988 | Ruderian | 401/2 |
| 5,188,096 A | * | 2/1993 | Yoo | 601/57 |
| 5,413,551 A | * | 5/1995 | Wu | 601/131 |
| 5,797,860 A | * | 8/1998 | Moriyasu | 601/30 |

FOREIGN PATENT DOCUMENTS

GB 2124084 A * 2/1984 ............ A61H/7/00

* cited by examiner

Primary Examiner—Danton D. DeMille
Assistant Examiner—Quang D Thanh
(74) Attorney, Agent, or Firm—Troxell Law Office PLLC

(57) ABSTRACT

A massage bead structure with heat application effect, more especially a press bead disposed with a vibrating wave-making massage apparatus for heat application, mainly has a semi-circular bead formed by a round canopy case body embedded with a vibrating wave generator therein and clamped outwardly with a heating piece composed by a ceramic-made electric resistance of positive temperature coefficient; the entire structure is inserted and connected to a leather mat plane in the shape of a fabric piece and formed into a plurality of beads arranged in rows; the heat wave produced from the said heat generator and transmitted through the round canopy case body is capable of synchronously massaging and being applied to the acupoint portion to obtain the complementary effect of physical therapy.

2 Claims, 5 Drawing Sheets

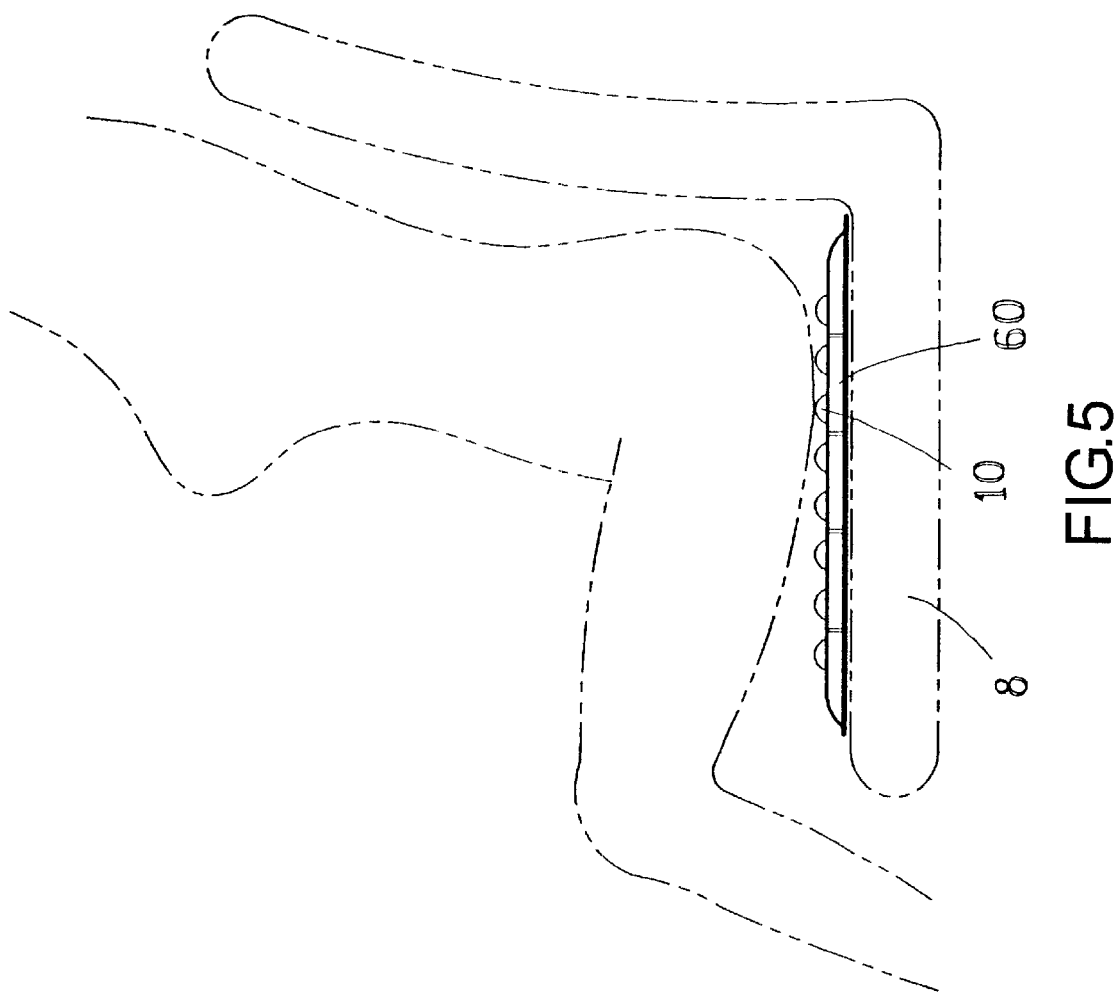

MESSAGE BEAD WITH HEAT APPLICATION EFFECT

BACKGROUND OF THE INVENTION

1) Field of the Invention

The present invention relates to a massage bead structure with heat application effect, more especially to a massage bead structure capable of obtaining heat application effect while massaging the user's limbs or external skin at the same time, mainly comprises a vibrating wave generator connected inside a round canopy case body of a formed bead and a heat generator disposed inbetween for generating heat wave through a ceramic-made electric resistance of positive temperature coefficient; the heat radiation wave generated by the heat generator can be directly used for contacting with the skin.

2) Description of the Prior Art

The common massage pad applied for physical therapy usually has a leather mat plane with a plurality of massage beads disposed convexedly in the upper aspect thereof; the vibration is formed by embedding a vibration motor or other vibration wave generators of similar applicative techniques inside the said bead; after the vibrating wave is transmitted to the bead, the entire bead body forms vibrating wave radiation and directly works onto the acupoint position on the skin; the applied styles can be in various forms of a belly girdle, a limb bandage, a shoulder pad or a mat; however, the acupoint on the human body is formed by crossed capillaries; therefore, in order to improve smooth blood vitalization so as to make blood vessels obtain smooth blood circulation, the massage methods added with proper temperature can achieve complementary therapeutic effect; furthermore, the common auxiliary apparatuses for heated therapeutic effect are formed by using extra heating pad of an electric blanket or chemical apparatuses without directly applying the bead, therefore the transmission of the heat radiation wave can't directly work at the acupoint position.

SUMMARY OF THE INVENTION

In view of the request of directly working at the acupoint and the necessary safety condition required by the said heat generator, the present invention uses a heat generator comprised by a ceramic-made electric resistance of positive temperature coefficient disposed between the vibrating wave generator and the inner surface of the case body; through the position adjacent to the case body, the obtained heat radiation wave can be transmitted directly to the working acupoint position directly through the case body to achieve the complementary and physically therapeutic effect.

To enable a further understanding of the structural features and the technical contents, the brief description of the drawings below is followed by the detailed description of the preferred embodiment.

BRIEF DESCRIPTION OF THE DRAWINGS

FIG. 5 is an additional exemplary embodiment of the present invention.

DETAILED DESCRIPTION OF THE PREFERRED EMBODIMENTS

The present invention of a massage bead structure with heat application effect mainly provides a massage bead structure capable of directly generating heat radiation wave on the bead body to directly work at the depressed acupoint position.

Figure 1:
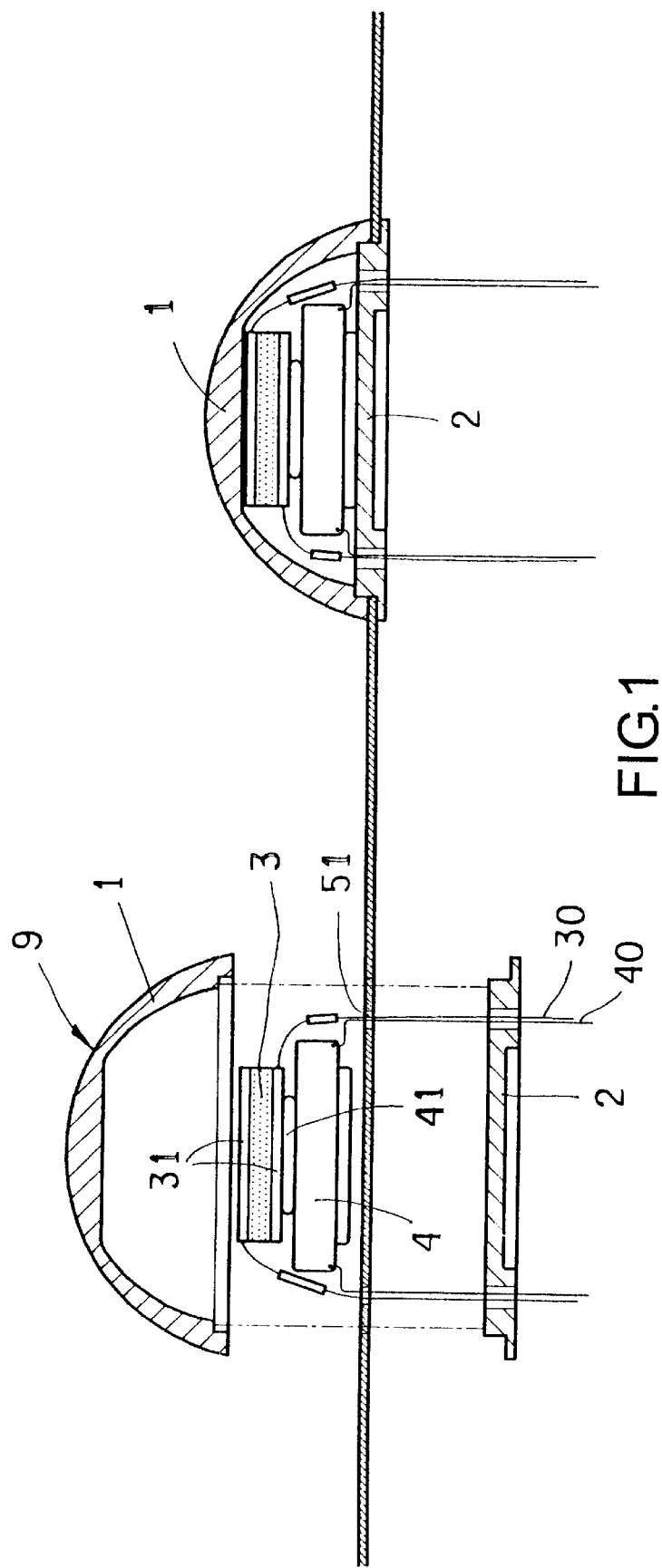
FIG. 1 is a cross-sectional drawing of the assembled present invention.
Figure 2:
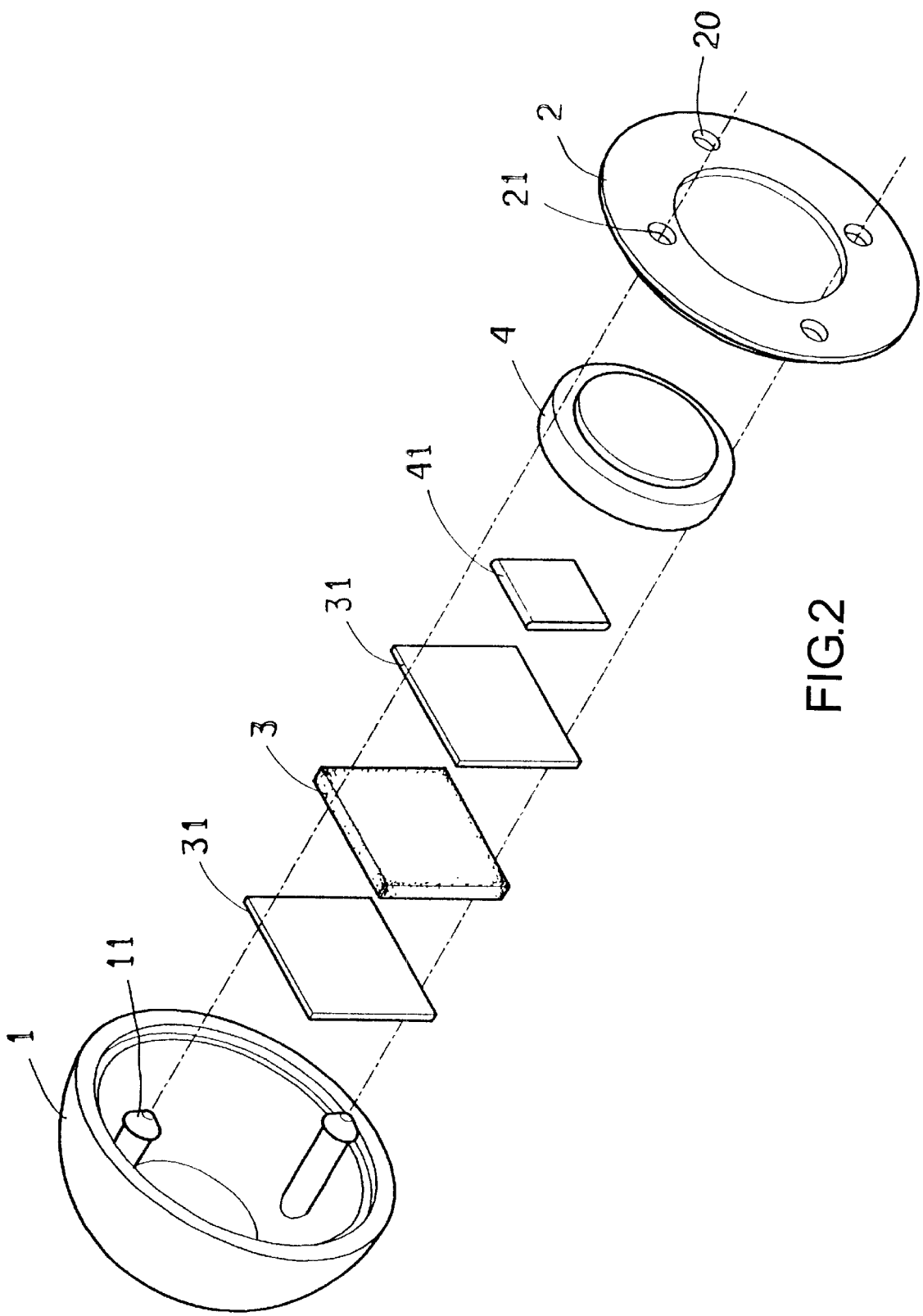
FIG. 2 is an exploded and pictorial drawing of the application the main elements of the present invention.

Referring to FIGS. 1 and 2, the present invention mainly comprises a round canopy case body (1) inserted downwardly by a bottom cover (2) with a mat plane (5) spaced inbetween to make the case body (1) be assembled on the mat plane (5); wherein, a vibrating wave generator (4) is disposed in the lower aspect inside the said case body (1); a heat generator (3) formed by a ceramic-made electric resistance of positive temperature coefficient is disposed between the upper surface of the said vibrating wave generator (4) outwardly opposing to the inner surface of the case body (1); the said heat generator (3) is respectively communicated with the electric power by means of a electrode tab (31) and a guide wire (30); the vibrating wave generator (4) also communicates with the electric power through a guide wire (40); the guide wires (30, 40) respectively penetrate through a through hole (51) disposed on the mat plane (5); the assembled case body (1) forms a semi-circular bead (10); referring to FIG. 2, basically, the said case body (1) is longitudinally disposed with a clip tenon (11); the foot end of the clip tenon (11) works onto a tenon hole (21) disposed on the bottom cover (2); the bottom cover (2) is disposed with a wire hole (20) for the guide wires (30, 40) to go through, as shown in FIG. 1; a resilient push-against member (41) is disposed at the position on the vibrating wave generator (4) upwardly opposing to the heat generator (3); after the round canopy case body (1) and the bottom cover (2) are inserted, the assembled force thereof, through an expanding force made by the function of the resilient push-against member (41), presses against the electrode tab (31) to clamp the said heat generator (3) upwardly and downwardly to maintain a good electrical conduction.

Figure 3:
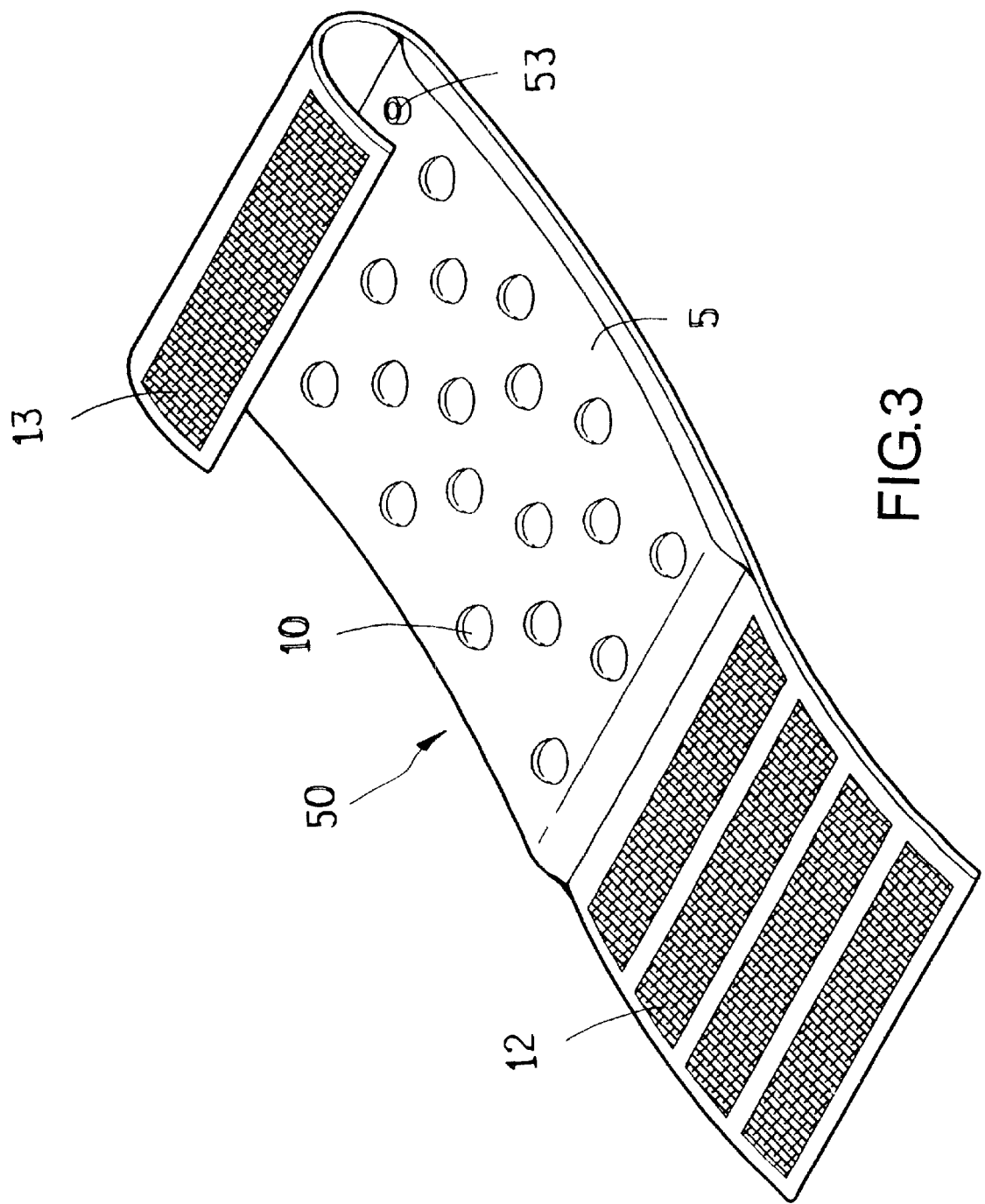
FIG. 3 is a pictorial drawing of an applicative example of the present invention.
Figure 4:
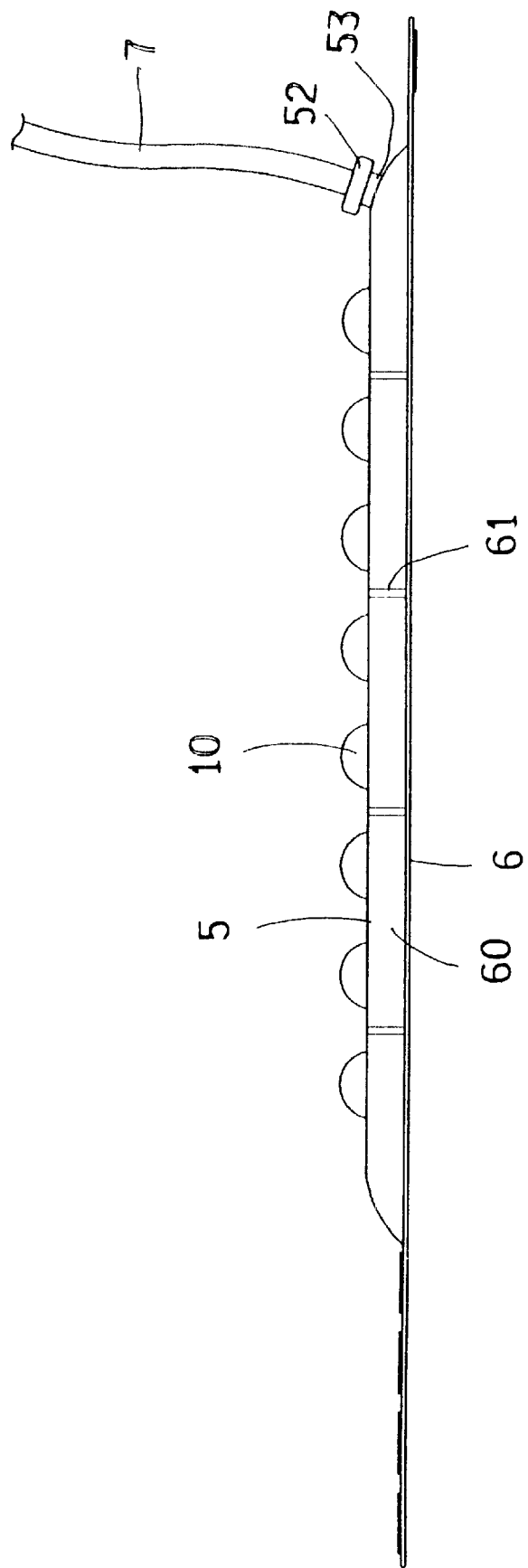
FIG. 4 is another exemplary embodiment of the present invention.

Referring to FIG. 3, the formed bead (10), as shown in FIGS. 1 and 2, are assembled on the mat plane (5) in a plurality of rows; the front and the back ends of the mat plane (5) are respectively formed into a hook fastener (12) and a loop fastener (13); the lower aspect of the mat plane is spaced by a mat bottom (6) with an air chamber (60) composed inbetween; the mat plane (5) and the mat bottom (6) are connected by the said air chamber (60) by means of a segmented connecting band (61); referring to FIG. 4, one side of the said mat plane (5) is disposed with an inserted spout (53) providing communication of a joint (52) disposed on a guide tube (7) for conducting the pressured air inwardly to fill the air chamber (60); the cushioning bottom (50) comprised by the mat plane (5) and the mat bottom (6) forms a function of an air cell to store the pressure, as the application of sitting-down pressure shown in FIG. 5.

Referring to FIG. 5, the entire structure can be flatly placed at the position in the upper aspect of a seat pad (8) of a chair and the air chamber (60) is filled with air; therefore, the present invention can be applied to the upper aspects of a hard or a soft seat pad; the existence of the air chamber (60) allows a guide tube (7) to conduct in pressure, as shown in FIG. 4; if the air is released intermittently or the filled air can be adjusted to get high or low pressure, the sitting-down pose can be moved closely to the position of the center of gravity; when the air pressure is less, the pushing functional force on the acupoint from the bead (10) located adjacent to the human body position of the center of gravity changes correspondingly to the amount of the air conducted in; even a segmental and intermittent way of communicating the air pressure is used to massage alternatively the human skin in high or low force; the said heat wave is generated directly from the outer surface of the said bead (10), therefore, when the air fills in a high pressure, the heat wave will be transmitted into the skin more intensively; when the air pressure is released, according to the unequal curved lines of the human body surface, the unequal heat transmitting effects happen due to the unequal sitting-down pressure.

Another objective of the present invention is to spread a layer of converting layer (9) of distant infrared ray wavelength on the outmost layer of the said round canopy case body (1), as shown in FIG. 1; by using the effect of the converting layer (9), formed hear radiation wave can be converted respectively to a distant infrared ray wavelength; since the wave form of the said distant infrared ray wavelength is easier in shooting into the water, the cells or the blood of the skin thereby can obtain the resonant oscillation of equal frequency to vitalize the molecule in the cells and improve the blood circulation to be more smooth.

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:

1. A massage bead structure with a plurality of beads for physical application, heat application effect and massage, comprising: each bead including a round canopy case body spaced by a mat plane and assembled to a bottom cover to form a massage bead; a vibrating generator disposed inside the case body; a heat generator of a ceramic electric resistance having a positive temperature coefficient disposed on an upper aspect of the vibrating generator opposite to an inner surface portion of the vibrating generator; and a resilient member disposed between the vibrating generator and the heat generator.

2. The massage bead structure according to claim 1, wherein, the case body is attached to the bottom cover by a clip tenon on the case body engaging a tenon hole in the bottom cover.

\* \* \* \* \*